US007052680B2

(12) United States Patent
Rabinowitz et al.

(10) Patent No.: US 7,052,680 B2
(45) Date of Patent: *May 30, 2006

(54) DELIVERY OF COMPOUNDS FOR THE TREATMENT OF PARKINSONS THROUGH AN INHALATION ROUTE

(75) Inventors: Joshua D. Rabinowitz, Mountain View, CA (US); Alejandro C. Zaffaroni, Atherton, CA (US)

(73) Assignee: Alexza Pharmaceuticals, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/816,567

(22) Filed: Apr. 1, 2004

(65) Prior Publication Data

US 2004/0185008 A1    Sep. 23, 2004

Related U.S. Application Data

(63) Continuation of application No. 10/153,139, filed on May 20, 2002, now Pat. No. 6,814,954.

(60) Provisional application No. 60/317,479, filed on Sep. 5, 2001, provisional application No. 60/294,203, filed on May 24, 2001.

(51) Int. Cl.
*A61K 9/12* (2006.01)
*A61K 9/14* (2006.01)
*A61M 15/00* (2006.01)

(52) U.S. Cl. .......................... 424/45; 424/46; 424/489; 424/499; 128/200.14; 128/200.24; 128/203.15; 514/958

(58) Field of Classification Search .................. 424/45, 424/46, 43, 489, 789, 499; 514/220, 252, 514/958; 128/200.24, 200.14, 203.15
See application file for complete search history.

(56) References Cited

U.S. PATENT DOCUMENTS

| 3,219,533 | A | 11/1965 | Mullins |
|---|---|---|---|
| 3,560,607 | A | 2/1971 | Hartley et al. |
| 3,949,743 | A | 4/1976 | Shanbrom |
| 3,982,095 | A | 9/1976 | Robinson |
| 4,141,369 | A | 2/1979 | Burruss |
| RE30,285 | E | 5/1980 | Babington |
| 4,303,083 | A | 12/1981 | Buruss, Jr. |
| 4,474,191 | A | 10/1984 | Steiner |
| 4,484,576 | A | 11/1984 | Albarda |
| 4,566,451 | A | 1/1986 | Badewien |
| 4,708,151 | A | 11/1987 | Shelar |
| 4,734,560 | A | 3/1988 | Bowen |
| 4,735,217 | A | 4/1988 | Gerth |
| 4,819,665 | A | 4/1989 | Roberts et al. |
| 4,848,374 | A | 7/1989 | Chard et al. |
| 4,853,517 | A | 8/1989 | Bowen |
| 4,895,719 | A | 1/1990 | Radhakrishnun et al. |
| 4,906,417 | A | 3/1990 | Gentry |
| 4,917,119 | A | 4/1990 | Potter et al. |
| 4,924,883 | A | 5/1990 | Perfetti et al. |
| 4,941,483 | A | 7/1990 | Ridings |
| 4,963,289 | A | 10/1990 | Ortiz et al. |
| 5,042,509 | A | 8/1991 | Banerjee et al. |
| 5,049,389 | A | 9/1991 | Radhakrishnan |
| 5,060,671 | A | 10/1991 | Counts et al. |
| 5,099,861 | A | 3/1992 | Clearman et al. |
| 5,135,009 | A | 8/1992 | Muller et al. |
| 5,144,962 | A | 9/1992 | Counts et al. |
| 5,146,915 | A | 9/1992 | Montgomery |
| 5,224,498 | A | 7/1993 | Deevi et al. |
| 5,345,951 | A | 9/1994 | Serrano et al. |
| 5,366,770 | A | 11/1994 | Wang |
| 5,388,574 | A | 2/1995 | Ingebrethsen |
| 5,456,247 | A | 10/1995 | Schilling et al. |
| 5,511,726 | A | 4/1996 | Greenspan et al. |
| 5,544,646 | A | 8/1996 | Lloyd et al. |
| 5,564,442 | A | 10/1996 | MacDonald et al. |
| 5,592,934 | A | 1/1997 | Thwaites |
| 5,605,146 | A | 2/1997 | Sarela |
| 5,649,554 | A | 7/1997 | Sprinkel et al. |
| 5,655,523 | A | 8/1997 | Hodson et al. |
| 5,666,977 | A | 9/1997 | Higgins et al. |
| 5,694,919 | A | 12/1997 | Rubsamen et al. |

(Continued)

FOREIGN PATENT DOCUMENTS

EP    0 358 114    3/1990

(Continued)

OTHER PUBLICATIONS

Office Action mailed Dec. 4, 2003 for U.S. Appl. No. 10/057,198, filed Oct. 26, 2001, "Method And Device For Delivering A Physiologically Active Compound".

(Continued)

*Primary Examiner*—Sreeni Padmanashan
*Assistant Examiner*—Mina Haghighatian
(74) *Attorney, Agent, or Firm*—Swanson & Bratschun, LLC; William L. Leschensky

(57) ABSTRACT

The present invention relates to the delivery of antiparkinsons drugs through an inhalation route. In a method aspect of the present invention, an antiparkinsons drug is administered to a patient through an inhalation route. The method comprises: a) heating a thin layer of an antiparkinsons drug on a solid support to form a vapor; and, b) passing air through the heated vapor to produce aerosol particles having less than 5% drug degradation products. In a kit aspect of the present invention, a kit for delivering an antiparkinsons drug through an inhalation route is provided which comprises: a) a thin coating of a an antiparkinsons drug composition; and, b) a device for dispending said thin coating as a condensation aerosol.

**40

U.S. PATENT DOCUMENTS

| | | | |
|---|---|---|---|
| 5,735,263 | A | 4/1998 | Rubsamen et al. |
| 5,738,865 | A | 4/1998 | Baichwal et al. |
| 5,743,251 | A | 4/1998 | Howell |
| 5,758,637 | A | 6/1998 | Ivri et al. |
| 5,819,756 | A | 10/1998 | Mielordt |
| 5,840,246 | A | 11/1998 | Hammons et al. |
| 5,855,913 | A | 1/1999 | Hanes et al. |
| 5,874,481 | A | 2/1999 | Weers |
| 5,894,841 | A | 4/1999 | Voges |
| 5,915,378 | A | 6/1999 | Lloyd et al. |
| 5,918,595 | A | 7/1999 | Olsson et al. |
| 5,934,272 | A | 8/1999 | Lloyd et al. |
| 5,957,124 | A | 9/1999 | Lloyd et al. |
| 5,960,792 | A | 10/1999 | Lloyd et al. |
| 5,993,805 | A | 11/1999 | Sutton et al. |
| 6,041,777 | A * | 3/2000 | Faithfull et al. ....... 128/200.24 |
| 6,051,566 | A | 4/2000 | Bianco |
| 6,090,212 | A | 7/2000 | Mahawili |
| 6,095,134 | A | 8/2000 | Sievers et al. |
| 6,095,153 | A | 8/2000 | Kessler et al. |
| 6,102,036 | A | 8/2000 | Slutsky et al. |
| 6,131,570 | A | 10/2000 | Schuster et al. |
| 6,136,295 | A | 10/2000 | Edwards et al. |
| 6,155,268 | A | 12/2000 | Takeuchi |
| 6,158,431 | A | 12/2000 | Poole |
| 6,234,167 | B1 | 5/2001 | Cox et al. |
| 6,241,969 | B1 | 6/2001 | Saidi et al. |
| 6,255,334 | B1 | 7/2001 | Sands |
| 6,313,176 | B1 | 11/2001 | Ellinwood, Jr. et al. |
| 6,506,762 | B1 | 1/2003 | Horvath et al. |
| 6,514,482 | B1 * | 2/2003 | Bartus et al. ................. 424/45 |
| 6,591,839 | B1 | 7/2003 | Meyer et al. |
| 6,632,047 | B1 | 10/2003 | Vinegar |
| 6,701,922 | B1 | 3/2004 | Hindle et al. |
| 6,772,756 | B1 | 8/2004 | Shayan |
| 6,814,954 | B1 * | 11/2004 | Rabinowitz et al. .......... 424/45 |
| 2001/0020147 | A1 | 9/2001 | Staniforth et al. |
| 2002/0037828 | A1 | 3/2002 | Wilson et al. |
| 2002/0058009 | A1 | 5/2002 | Bartus et al. |
| 2002/0086852 | A1 | 7/2002 | Cantor |
| 2002/0112723 | A1 | 8/2002 | Schuster et al. |
| 2002/0117175 | A1 | 8/2002 | Kottayil et al. |
| 2002/0176841 | A1 | 11/2002 | Barker et al. |
| 2003/0000518 | A1 | 1/2003 | Rabinowitz et al. |
| 2003/0004142 | A1 | 1/2003 | Prior et al. |
| 2003/0005924 | A1 | 1/2003 | Rabinowitz et al. |
| 2003/0005925 | A1 | 1/2003 | Hale et al. |
| 2003/0007933 | A1 | 1/2003 | Rabinowitz et al. |
| 2003/0007934 | A1 | 1/2003 | Rabinowitz et al. |
| 2003/0012737 | A1 | 1/2003 | Rabinowitz et al. |
| 2003/0012738 | A1 | 1/2003 | Rabinowitz et al. |
| 2003/0012740 | A1 | 1/2003 | Rabinowitz et al. |
| 2003/0015189 | A1 | 1/2003 | Rabinowitz et al. |
| 2003/0015190 | A1 | 1/2003 | Rabinowitz et al. |
| 2003/0015196 | A1 | 1/2003 | Hodges et al. |
| 2003/0017114 | A1 | 1/2003 | Rabinowitz et al. |
| 2003/0017115 | A1 | 1/2003 | Rabinowitz et al. |
| 2003/0017116 | A1 | 1/2003 | Rabinowitz et al. |
| 2003/0017117 | A1 | 1/2003 | Rabinowitz et al. |
| 2003/0017118 | A1 | 1/2003 | Rabinowitz et al. |
| 2003/0017119 | A1 | 1/2003 | Rabinowitz et al. |
| 2003/0017120 | A1 | 1/2003 | Rabinowitz et al. |
| 2003/0021753 | A1 | 1/2003 | Rabinowitz et al. |
| 2003/0021754 | A1 | 1/2003 | Rabinowitz et al. |
| 2003/0021755 | A1 | 1/2003 | Hale et al. |
| 2003/0032638 | A1 | 2/2003 | Kim et al. |
| 2003/0035776 | A1 | 2/2003 | Hodges et al. |
| 2003/0062042 | A1 | 4/2003 | Wensley et al. |
| 2003/0091511 | A1 | 5/2003 | Rabinowitz et al. |
| 2003/0138382 | A1 | 7/2003 | Rabinowitz |
| 2003/0206869 | A1 | 11/2003 | Rabinowitz et al. |
| 2003/0209240 | A1 | 11/2003 | Hale et al. |
| 2004/0009128 | A1 | 1/2004 | Rabinowitz et al. |
| 2004/0010148 | A1 | 1/2004 | Kirane et al. |
| 2004/0016427 | A1 * | 1/2004 | Byron et al. ........... 128/200.14 |
| 2004/0096402 | A1 | 5/2004 | Hodges et al. |
| 2004/0099269 | A1 | 5/2004 | Hale et al. |
| 2004/0105818 | A1 | 6/2004 | Hale et al. |
| 2004/0105819 | A1 | 6/2004 | Hale et al. |
| 2004/0126326 | A1 | 7/2004 | Rabinowitz et al. |
| 2004/0126327 | A1 | 7/2004 | Rabinowitz et al. |
| 2004/0126328 | A1 | 7/2004 | Rabinowitz et al. |
| 2004/0126329 | A1 | 7/2004 | Rabinowitz et al. |
| 2004/0127481 | A1 | 7/2004 | Rabinowitz et al. |
| 2004/0127490 | A1 | 7/2004 | Rabinowitz et al. |
| 2004/0156788 | A1 | 8/2004 | Rabinowitz et al. |
| 2004/0156789 | A1 | 8/2004 | Rabinowitz et al. |
| 2004/0156790 | A1 | 8/2004 | Rabinowitz et al. |
| 2004/0156791 | A1 | 8/2004 | Rabinowitz et al. |

FOREIGN PATENT DOCUMENTS

| | | |
|---|---|---|
| EP | 1 080 720 | 7/2001 |
| EP | 0 606 486 | 8/2001 |
| GB | 502 761 | 3/1939 |
| WO | WO 85/00520 | 2/1985 |
| WO | WO 91/07947 | 6/1991 |
| WO | WO 94/09842 | 5/1994 |
| WO | WO 96/09846 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 97/27804 | 8/1997 |
| WO | WO 97/36574 | 10/1997 |
| WO | WO 98/22170 | 5/1998 |
| WO | WO 98/31346 | 7/1998 |
| WO | WO 98/36651 | 8/1998 |
| WO | WO 99/16419 | 4/1999 |
| WO | WO 99/64094 | 12/1999 |
| WO | WO 00/00176 | 1/2000 |
| WO | WO 00/00215 | 1/2000 |
| WO | WO 00/27363 | 5/2000 |
| WO | WO 00/29053 | 5/2000 |
| WO | WO 00/47203 | 9/2000 |
| WO | WO 00/64940 | 11/2000 |
| WO | WO 00/66084 | 11/2000 |
| WO | WO 00/66206 | 11/2000 |
| WO | WO 00/76673 | 12/2000 |
| WO | WO 01/05459 | 1/2001 |
| WO | WO 02/24158 | 3/2002 |
| WO | WO 03/037412 | 5/2003 |

OTHER PUBLICATIONS

Office Action mailed Jan. 12, 2005 for U.S. Appl. No. 10/057,197, filed Oct. 26, 2001, "Aerosol Generating Device And Method".

Office Action mailed Jun. 3, 2004 for U.S. Appl. No. 10/057,197, filed Oct. 26, 2001, "Aerosol Generating Device And Method".

Office Action mailed Dec. 15, 2003 for U.S. Appl. No. 10/057,197, filed Oct. 26, 2001, "Aerosol Generating Device And Method".

Office Action mailed Feb. 27, 2004 for U.S. Appl. No. 10/146,080, filed May 13, 2002, "Aerosol Forming Device For Use In Inhalation Therapy".

U.S. Appl. No. 10/057,198, filed Oct. 26, 2001, Lloyd et al.

U.S. Appl. No. 10/302,614, filed Nov. 21, 2002, Lu

U.S. Appl. No. 10/146,088, filed May 13, 2002, Hale et al.

U.S. Appl. No. 10/280,315, filed Oct. 25, 2002, Shen.

U.S. Appl. No. 10/322,227, filed Dec. 17, 2002, Novack et al.
U.S. Appl. No. 10/442,385, filed May 20, 2003, Cross et al.
U.S. Appl. No. 10/719,540, filed Nov. 20, 2003, Hale et al.
U.S. Appl. No. 10/850,895, filed May 20, 2004, Damani et al.
U.S. Appl. No. 10/851,429, filed May 20, 2004, Hale et al.
U.S. Appl. No. 10/851,883, filed May 20, 2004, Hale et al.
U.S. Appl. No. 10/851,432, filed May 20, 2004, Hale et al.
U.S. Appl. No. 10/861,554, filed Jun. 03, 2004, Cross et al.
U.S. Appl. No. 10/851,018, filed May 20, 2004, Hale et al.
U.S. Appl. No. 10/917,735, filed Aug. 12, 2004, Hale et al.
U.S. Appl. No. 10/917,720, filed Aug. 12, 2004, Hale et al.
U.S. Appl. No. 10/912,417, filed Aug. 4, 2004, Bennett et al.
U.S. Appl. No. 10/633,876, filed Aug. 4, 2003, Hale et al.
U.S. Appl. No. 10/633,877, filed Aug. 4, 2003, Hale et al.
U.S. Appl. No. 10/749,537, filed Dec. 30, 2003, Rabinowitz et al.
U.S. Appl. No. 10/749,539, filed Dec. 30, 2003, Rabinowitz et al.
U.S. Appl. No. 10/766,149, filed Jan. 27, 2004, Rabinowitz et al.
U.S. Appl. No. 10/766,279, filed Jan. 27, 2004, Rabinowitz et al.
U.S. Appl. No. 10/766,566, filed Jan. 27, 2004, Rabinowitz et al.
U.S. Appl. No. 10/766,574, filed Jan. 27, 2004, Rabinowitz et al.
U.S. Appl. No. 10/766,634, filed Jan. 27, 2004, Rabinowitz et al.
U.S. Appl. No. 10/766,647, filed Jan. 27, 2004, Rabinowitz et al.
U.S. Appl. No. 10/767,115, filed Jan. 28, 2004, Rabinowitz et al.
U.S. Appl. No. 10/768,205, filed Jan. 29, 2004, Rabinowitz et al.
U.S. Appl. No. 10/768,220, filed Jan. 29, 2004, Rabinowitz et al.
U.S. Appl. No. 10/768,281, filed Jan. 29, 2004, Rabinowitz et al.
U.S. Appl. No. 10/768,293, filed Jan. 29, 2004, Rabinowitz et al.
U.S. Appl. No. 10/769,046, filed Jan. 30, 2004, Rabinowitz et al.
U.S. Appl. No. 10/769,051, filed Jan. 30, 2004, Rabinowitz et al.
U.S. Appl. No. 10/769,157, filed Jan. 29, 2004, Rabinowitz et al.
U.S. Appl. No. 10/769,197, filed Jan. 29, 2004, Rabinowitz et al.
U.S. Appl. No. 10/775,583, filed Feb. 9, 2004, Rabinowitz et al.
U.S. Appl. No. 10/775,586, filed Feb. 9, 2004, Rabinowitz et al.
U.S. Appl. No. 10/791,915, filed Mar. 3, 2004, Hale et al.
U.S. Appl. No. 10/792,001, filed Mar. 3, 2004, Rabinowitz et al.
U.S. Appl. No. 10/792,012, filed Mar. 3, 2004, Hale et al.
U.S. Appl. No. 10/792,013, filed Mar. 3, 2004, Rabinowitz et al.
U.S. Appl. No. 10/792,096, filed Mar. 3, 2004, Hale et al.
U.S. Appl. No. 10/792,239, filed Mar. 3, 2004, Hale et al.
U.S. Appl. No. 10/813,721, filed Mar. 31, 2004, Rabinowitz et al.
U.S. Appl. No. 10/813,722, filed Mar. 31, 2004, Rabinowitz et al.
U.S. Appl. No. 10/814,690, filed Mar. 31, 2004, Rabinowitz et al.
U.S. Appl. No. 10/814,998, filed Mar. 31, 2004, Rabinowitz et al.
U.S. Appl. No. 10/815,527, filed Apr. 1, 2004, Rabinowitz et al.
U.S. Appl. No. 10/816,407, filed Apr. 1, 2004, Rabinowitz et al.
U.S. Appl. No. 10/816,492, filed Apr. 1, 2004, Rabinowitz et al.
U.S. Appl. No. 10/912,462, filed Aug. 4, 2004, Hale et al.
Bennett, R.L. et al. (1981). "Patient-Controlled Analgesia: A New Concept of Postoperative Pain Relief," *Annual Surg.* 195(6):700-705.
Carroll, M.E. et al. (1990), "Cocaine-base smoking in rhesus monkeys: reinforcing and physiological effects,"*Psychopharmacology* (Berl). 102:443-450.
Clark, A. and Byron, P. (1986). "Dependence of Pulmonary Absorption Kinetics on Aerosol Particle Size,"*Z. Erkrank.* 166:13-24.
Darquenne, C. et al. (1997). "Aerosol Dispersion in Human Lung: Comparison Between Numerical Simulations and Experiments for Bolus Tests," *American Physiological Society.* 966-974.
Database Biosis "Online!" Biosciences Information Service, Philadelphia, PA 1979, Knight, V. et al., "Amantadine aerosol in humans", database accession No. PREV 198069035552 abstract, &Antimicrobial Agents and Chemotherapy 16(5):572-578.
Database Biosis "Online!" Biosciences Information Service, Philadelphia, PA 1979, Wilson. S.Z. et al., "Amatadine Aerosol Particle Aerosol Generation and Delivery to Man" Database accession No. PREV198069008137, abstract & Proceedings of the Society for Experimental Biology and Medicine 161(3):350-354.
Davies, C.N. et al. (May 1972). "Breathing of Half-Micron Aerosols," *Journal of Applied Physiology.* 32(5):591-600.
Dershwitz, M., M.D., et al. (Sep. 2000). "Pharmacokinetics and Pharmacodynamics of Inhaled versus Intravenous Morphine in Healthy Volunteers," *Anesthesiology.* 93(3): 619-628.
Finlay, W.H. (2001). "The Mechanics of Inhaled Pharmaceutical Aerosols", Academic Press: San Diego Formula 2.39. pp. 3-14 (Table of Contents). pp. v-viii.
Gonda,I. (1991). "Particle Deposition in the Human Respiratory Tract," Chapter 176, *The Lung: Scientific Foundations.* Crystal R.G. and West, J.B. (eds.), Raven Publishers, New York. pp. 2289-2294.
Hatsukami D, et al. (May 1990) "A method for delivery of precise doses of smoked cocaine-base to humans." *Pharmacology Biochemistry & Behavior.* 36(1):1-7.
Heyder, J. et al. (1986). "Deposition of Particles in the Human Respiratory Tract in the Size Range 0.005-15 μm," *J. Aerosol Sci.* 17(5):811-822.
Huizer, H., "Analytical studies on illicit heron. V. Efficacy of volatilization during heroin smoking." *Pharmaceutisch Weekblad Scientific Edition* (1987). 9(4):203-211.
Hurt, R.D., MD and Robertson, C.R., PhD, (Oct. 1998). "Prying Open the Door to the Tobacco Industry's Secrets About Nicotine: The Minnesota Tobacco Trial," *JAMA* 280(13):1173-1181.
Lichtman, A.H. et al. (1996). "Inhalation Exposure to Volatilized Opioids Produces Antinociception in Mice," Journal of Pharmacology and Experimental Therapeutics. 279(1):69-76.

Martin, B.R. and Lue, L.P. (May/Jun. 1989). "Pyrolysis and Volatilization of Cocaine," *Journal of Analytical Toxicology* 13:158-162.

Mattox, A.J. and Carroll, M.E., (1996). "Smoked heroin self-administration in rhesus monkeys," *Psychopharmacology*, 125:195-201.

Meng, Y. et al. "Inhalation Studies With Drugs of Abuse," *NIDA Research Monograph*, (1997) 173:201-224.

Meng, Y., et al. (1999). "Pharmacological effects of methamphetamine and other stimulants via inhalation exposure," *Drug and Alcohol Dependence*. 53:111-120.

Office Action mailed Aug. 13, 2003 for U.S. Appl. No. 10/153,313, filed May 21, 2002, "Delivery of Benzodiazepines Through an Inhalation Route".

Pankow, J.F. et al. (1997). "Conversion of Nicotine in Tobacco Smoke to Its Volatile and Available Free-Base Form Through the Action of Gaseous Ammonia," *Envron. Sci. Technol*. 31:2428-2433.

Pankow, J. (Mar. 2000). ACS Conference—San Francisco—Mar. 26, 2000. Chemistry of Tobacco Smoke. pp. 1-8.

Seeman, J. et al. (1999). "The Form of Nicotine in Tobacco. Thermal Transfer of Nicotine and Nicotine Acid Salts to Nicotine in the Gas Phase," *J. Agric. Food Chem.* 47(12):5133-5145.

Sekine, H. and Nakahara, Y. (1987). "Abuse of Smoking Methamphetamine Mixed with Tobacco: 1. Inhalation Efficiency and Pyrolysis Products of Methamphetamine," *Journal of Forensic Science* 32(5);1271-1280.

Vapotronics, Inc. (1998) located at http://www.vapotronics.com.au/banner.htm., 11 pages, (visited on Jun. 5, 2000).

Ward, M.E. MD, et al. (Dec. 1997). "Morphine Pharmacokinetics after Pulmonary Administration from a Novel Aerosol Delivery System," *Clinical Pharmacology & Therapeutics* 62(6):596-609.

Wood, R.W. et al. (1996). "Generation of Stable Test Atmospheres of Cocaine Base and Its Pyrolyzate, Methylecgonidine, and Demonstration of Their Biological Activity." *Pharmacology Biochemistry & Behavior*. 55(2):237-248.

* cited by examiner

DELIVERY OF COMPOUNDS FOR THE TREATMENT OF PARKINSONS THROUGH AN INHALATION ROUTE

This application is a continuation of U.S. patent application Ser. No. 10/153,139, entitled "Delivery of Compounds for the Treatment of Parkinsons Through an Inhalation Route," filed May 20, 2002, now U.S. Pat. No. 6,814,954, Rabinowitz and Zaffaroni; which claims priority to U.S. provisional application Ser. No. 60/294,203 entitled "Thermal Vapor Delivery of Drugs," filed May 24, 2001, Rabinowitz and Zaffaroni, the entire disclosure of which is hereby incorporated by reference. This application further claims priority to U.S. provisional application Ser. No. 60/317,479 entitled "Aerosol Drug Delivery," filed Sep. 5, 2001, Rabinowitz and Zaffaroni, the entire disclosure of which is hereby incorporated by reference.

FIELD OF THE INVENTION

The present invention relates to the delivery of compounds for the treatment of Parkinsons through an inhalation route. Specifically, it relates to aerosols containing antiparkinsons drugs that are used in inhalation therapy.

BACKGROUND OF THE INVENTION

There are a number of compositions currently marketed for the treatment of Parkinsons. The compositions contain at least one active ingredient that provides for observed therapeutic effects. Among the active ingredients given in such antiparkinsons compositions are benzotropine, pergolide, ropinerole, amantadine and deprenyl.

It is desirable to provide a new route of administration for antiparkinsons drugs that rapidly produces peak plasma concentrations of the compounds. The provision of such a route is an object of the present invention.

SUMMARY OF THE INVENTION

The present invention relates to the delivery of compounds for the treatment of Parkinsons through an inhalation route. Specifically, it relates to aerosols containing antiparkinsons drugs that are used in inhalation therapy.

In a composition aspect of the present invention, the aerosol comprises particles comprising at least 5 percent by weight of an antiparkinsons drug. Preferably, the particles comprise at least 10 percent by weight of an antiparkinsons drug. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of an antiparkinson drug.

Typically, the aerosol has a mass of at least 10 µg. Preferably, the aerosol has a mass of at least 100 µg. More preferably, the aerosol has a mass of at least 200 µg.

Typically, the particles comprise less than 10 percent by weight of antiparkinson drug degradation products. Preferably, the particles comprise less than 5 percent by weight of antiparkinson drug degradation products. More preferably, the particles comprise less than 2.5, 1, 0.5, 0.1 or 0.03 percent by weight of antiparkinson drug degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the aerosol has an inhalable aerosol particle density greater than $10^6$ particles/mL. Preferably, the aerosol has an inhalable aerosol particle density greater than $10^7$ particles/mL or $10^8$ particles/mL.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.3.

Typically, the aerosol is formed by heating a composition containing an antiparkinson drug to form a vapor and subsequently allowing the vapor to condense into an aerosol.

In another composition aspect of the present invention, the aerosol comprises particles comprising at least 5 percent by weight of benzotropine, pergolide, ropinerole, amantadine or deprenyl. Preferably, the particles comprise at least 10 percent by weight of benzotropine, pergolide, ropinerole, amantadine or deprenyl. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of benzotropine, pergolide, ropinerole, amantadine or deprenyl.

Typically, the aerosol has a mass of at least 10 µg. Preferably, the aerosol has a mass of at least 100 µg. More preferably, the aerosol has a mass of at least 200 µg.

Typically, the particles comprise less than 10 percent by weight of benzotropine, pergolide, ropinerole, amantadine or deprenyl degradation products. Preferably, the particles comprise less than 5 percent by weight of benzotropine, pergolide, ropinerole, amantadine or deprenyl degradation products. More preferably, the particles comprise less than 2.5, 1, 0.5, 0.1 or 0.03 percent by weight of benzotropine, pergolide, ropinerole, amantadine or deprenyl degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, where the aerosol comprises benzotropine, the aerosol has an inhalable aerosol drug mass density of between 0.1 mg/L and 4 mg/L. Preferably, the aerosol has an inhalable aerosol drug mass density of between 0.2 mg/L and 3 mg/L. More preferably, the aerosol has an inhalable aerosol drug mass density of between 0.3 mg/L and 2 mg/L.

Typically, where the aerosol comprises pergolide, the aerosol has an inhalable aerosol drug mass density of between 0.01 mg/L and 2.5 mg/L. Preferably, the aerosol has an inhalable aerosol drug mass density of between 0.02 mg/L and 1 mg/L. More preferably, the aerosol has an inhalable aerosol drug mass density of between 0.05 mg/L and 0.5 mg/L.

Typically, where the aerosol comprises ropinerole, the aerosol has an inhalable aerosol drug mass density of between 0.02 mg/L and 4 mg/L. Preferably, the aerosol has an inhalable aerosol drug mass density of between 0.04 mg/L and 2 mg/L. More preferably, the aerosol has an inhalable aerosol drug mass density of between 0.10 mg/L and 1.0 mg/L.

Typically, where the aerosol comprises amantadine, the aerosol has an inhalable aerosol drug mass density of between 5 mg/L and 500 mg/L. Preferably, the aerosol has an inhalable aerosol drug mass density of between 10 mg/L and 200 mg/L. More preferably, the aerosol has an inhalable aerosol drug mass density of between 20 mg/L and 150 mg/L.

Typically, where the aerosol comprises deprenyl, the aerosol has an inhalable aerosol drug mass density of between 0.5 mg/L and 12.5 mg/L. Preferably, the aerosol has an inhalable aerosol drug mass density of between 1 mg/L and 10 mg/L. More preferably, the aerosol has an inhalable aerosol drug mass density of between 2 mg/L and 7.5 mg/L.

Typically, the aerosol has an inhalable aerosol particle density greater than $10^6$ particles/mL. Preferably, the aerosol has an inhalable aerosol particle density greater than $10^7$ particles/mL or $10^8$ particles/mL.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s). In certain embodiments the particles have an MMAD of from about 0.2 to about 3 microns.

Typically, the geometric standard deviation around the mass median aerodynamic diameter of the aerosol particles is less than 3.0. Preferably, the geometric standard deviation is less than 2.5. More preferably, the geometric standard deviation is less than 2.3.

Typically, the aerosol is formed by heating a composition containing benzotropine, pergolide, ropinerole, amantadine or deprenyl to form a vapor and subsequently allowing the vapor to condense into an aerosol.

In a method aspect of the present invention, an antiparkinson drug is delivered to a mammal through an inhalation route. The method comprises: a) heating a composition, wherein the composition comprises at least 5 percent by weight of an antiparkinson drug, to form a vapor; and, b) allowing the vapor to cool, thereby forming a condensation aerosol comprising particles, which is inhaled by the mammal. Preferably, the composition that is heated comprises at least 10 percent by weight of an antiparkinson drug. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an antiparkinson drug.

Typically, the particles comprise at least 5 percent by weight of an antiparkinson drug. Preferably, the particles comprise at least 10 percent by weight of an antiparkinson drug. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an antiparkinson drug.

Typically, the condensation aerosol has a mass of at least 10 μg. Preferably, the aerosol has a mass of at least 100 μg. More preferably, the aerosol has a mass of at least 200 μg.

Typically, the particles comprise less than 10 percent by weight of antiparkinson drug degradation products. Preferably, the particles comprise less than 5 percent by weight of antiparkinson drug degradation products. More preferably, the particles comprise 2.5, 1, 0.5, 0.1 or 0.03 percent by weight of antiparkinson drug degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.3.

Typically, the delivered aerosol has an inhalable aerosol particle density greater than $10^6$ particles/mL. Preferably, the aerosol has an inhalable aerosol particle density greater than $10^7$ particles/mL or $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second. More preferably, the aerosol is formed at a rate greater than $10^{10}$ inhalable particles per second.

Typically, the delivered condensation aerosol is formed at a rate greater than 0.5 mg/second. Preferably, the aerosol is formed at a rate greater than 0.75 mg/second. More preferably, the aerosol is formed at a rate greater than 1 mg/second, 1.5 mg/second or 2 mg/second.

Typically, the delivered condensation aerosol results in a peak plasma concentration of an antiparkinson drug in the mammal in less than 1 h. Preferably, the peak plasma concentration is reached in less than 0.5 h. More preferably, the peak plasma concentration is reached in less than 0.2, 0.1, 0.05, 0.02, 0.01, or 0.005 h (arterial measurement).

In another method aspect of the present invention, one of benzotropine, pergolide, ropinerole, amantadine or deprenyl is delivered to a mammal through an inhalation route. The method comprises: a) heating a composition, wherein the composition comprises at least 5 percent by weight of benzotropine, pergolide, ropinerole, amantadine or deprenyl, to form a vapor; and, b) allowing the vapor to cool, thereby forming a condensation aerosol comprising particles, which is inhaled by the mammal. Preferably, the composition that is heated comprises at least 10 percent by weight of benzotropine, pergolide, ropinerole, amantadine or deprenyl. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of benzotropine, pergolide, ropinerole, amantadine or deprenyl.

Typically the particles comprise at least 5 percent by weight of benzotropine, pergolide, ropinerole, amantadine or deprenyl. Preferably, the particles comprise at least 10 percent by weight of benzotropine, pergolide, ropinerole, amantadine or deprenyl. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of benzotropine, pergolide, ropinerole, amantadine or deprenyl.

Typically, the condensation aerosol has a mass of at least 10 μg. Preferably, the aerosol has a mass of at least 100 μg. More preferably, the aerosol has a mass of at least 200 μg.

Typically, the particles comprise less than 10 percent by weight of benzotropine, pergolide, ropinerole, amantadine or deprenyl degradation products. Preferably, the particles comprise less than 5 percent by weight of benzotropine, pergolide, ropinerole, amantadine or deprenyl degradation products. More preferably, the particles comprise 2.5, 1, 0.5, 0.1 or 0.03 percent by weight of benzotropine, pergolide, ropinerole, amantadine or deprenyl degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.3.

Typically, where the aerosol comprises benzotropine, the delivered aerosol has an inhalable aerosol drug mass density of between 0.1 mg/L and 4 mg/L. Preferably, the aerosol has an inhalable aerosol drug mass density of between 0.2 mg/L and 3 mg/L. More preferably, the aerosol has an inhalable aerosol drug mass density of between 0.3 mg/L and 2 mg/L.

Typically, where the aerosol comprises pergolide, the delivered aerosol has an inhalable aerosol drug mass density of between 0.01 mg/L and 2.5 mg/L. Preferably, the aerosol has an inhalable aerosol drug mass density of between 0.02 mg/L and 1 mg/L. More preferably, the aerosol has an inhalable aerosol drug mass density of between 0.05 mg/L and 0.5 mg/L.

Typically, where the aerosol comprises ropinerole, the delivered aerosol has an inhalable aerosol drug mass density of between 0.02 mg/L and 4 mg/L. Preferably, the aerosol has an inhalable aerosol drug mass density of between 0.04 mg/L and 2 mg/L. More preferably, the aerosol has an inhalable aerosol drug mass density of between 0.10 mg/L and 1.0 mg/L.

Typically, where the aerosol comprises amantadine, the delivered aerosol has an inhalable aerosol drug mass density of between 5 mg/L and 500 mg/L. Preferably, the aerosol has an inhalable aerosol drug mass density of between 10 mg/L and 200 mg/L. More preferably, the aerosol has an inhalable aerosol drug mass density of between 20 mg/L and 150 mg/L.

Typically, where the aerosol comprises deprenyl, the delivered aerosol has an inhalable aerosol drug mass density of between 0.5 mg/L and 12.5 mg/L. Preferably, the aerosol has an inhalable aerosol drug mass density of between 1 mg/L and 10 mg/L. More preferably, the aerosol has an inhalable aerosol drug mass density of between 2 mg/L and 7.5 mg/L.

Typically, the delivered aerosol has an inhalable aerosol particle density greater than $10^6$ particles/mL. Preferably, the aerosol has an inhalable aerosol particle density greater than $10^7$ particles/mL or $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second. More preferably, the aerosol is formed at a rate greater than $10^{10}$ inhalable particles per second.

Typically, the delivered condensation aerosol is formed at a rate greater than 0.5 mg/second. Preferably, the aerosol is formed at a rate greater than 0.75 mg/second. More preferably, the aerosol is formed at a rate greater than 1 mg/second, 1.5 mg/second or 2 mg/second.

Typically, where the condensation aerosol comprises benzotropine, between 0.1 mg and 4 mg of benzotropine are delivered to the mammal in a single inspiration. Preferably, between 0.2 mg and 3 mg of benzotropine are delivered to the mammal in a single inspiration. More preferably, between 0.3 mg and 2 mg of benzotropine are delivered to the mammal in a single inspiration.

Typically, where the condensation aerosol comprises pergolide, between 0.01 mg and 2.5 mg of pergolide are delivered to the mammal in a single inspiration. Preferably, between 0.02 mg and 1 mg of pergolide are delivered to the mammal in a single inspiration. More preferably, between 0.05 mg and 0.5 mg of pergolide are delivered to the mammal in a single inspiration.

Typically, where the condensation aerosol comprises ropinerole, between 0.02 mg and 4 mg of ropinerole are delivered to the mammal in a single inspiration. Preferably, between 0.04 mg and 2 mg of ropinerole are delivered to the mammal in a single inspiration. More preferably, between 0.1 mg and 1.0 mg of ropinerole are delivered to the mammal in a single inspiration.

Typically, where the condensation aerosol comprises amantadine, between 5 mg and 500 mg of amantadine are delivered to the mammal in a single inspiration. Preferably, between 10 mg and 200 mg of amantadine are delivered to the mammal in a single inspiration. More preferably, between 20 mg and 150 mg of amantadine are delivered to the mammal in a single inspiration.

Typically, where the condensation aerosol comprises deprenyl, between 0.5 mg and 12.5 mg of deprenyl are delivered to the mammal in a single inspiration. Preferably, between 1 mg and 10 mg of deprenyl are delivered to the mammal in a single inspiration. More preferably, between 2 mg and 7.5 mg of deprenyl are delivered to the mammal in a single inspiration.

Typically, the delivered condensation aerosol results in a peak plasma concentration of benzotropine, pergolide, ropinerole, amantadine or deprenyl in the mammal in less than 1 h. Preferably, the peak plasma concentration is reached in less than 0.5 h. More preferably, the peak plasma concentration is reached in less than 0.2, 0.1, 0.05, 0.02, 0.01, or 0.005 h (arterial measurement).

In a kit aspect of the present invention, a kit for delivering an antiparkinson through an inhalation route to a mammal is provided which comprises: a) a composition comprising at least 5 percent by weight of an antiparkinson drug; and, b) a device that forms an antiparkinson drug aerosol from the composition, for inhalation by the mammal. Preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an antiparkinson drug.

Typically, the device contained in the kit comprises: a) an element for heating the antiparkinson drug composition to form a vapor; b) an element allowing the vapor to cool to form an aerosol; and, c) an element permitting the mammal to inhale the aerosol.

In another kit aspect of the present invention, a kit for delivering benzotropine, pergolide, ropinerole, amantadine or deprenyl through an inhalation route to a mammal is provided which comprises: a) a composition comprising at least 5 percent by weight of benzotropine, pergolide, ropinerole, amantadine or deprenyl; and, b) a device that forms a benzotropine, pergolide, ropinerole, amantadine or deprenyl aerosol from the composition, for inhalation by the mammal. Preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of benzotropine, pergolide, ropinerole, amantadine or deprenyl.

Typically, the device contained in the kit comprises: a) an element for heating the benzotropine, pergolide, ropinerole, amantadine or deprenyl composition to form a vapor; b) an element allowing the vapor to cool to form an aerosol; and, c) an element permitting the mammal to inhale the aerosol.

DETAILED DESCRIPTION OF THE INVENTION

Definitions

Figure 1:
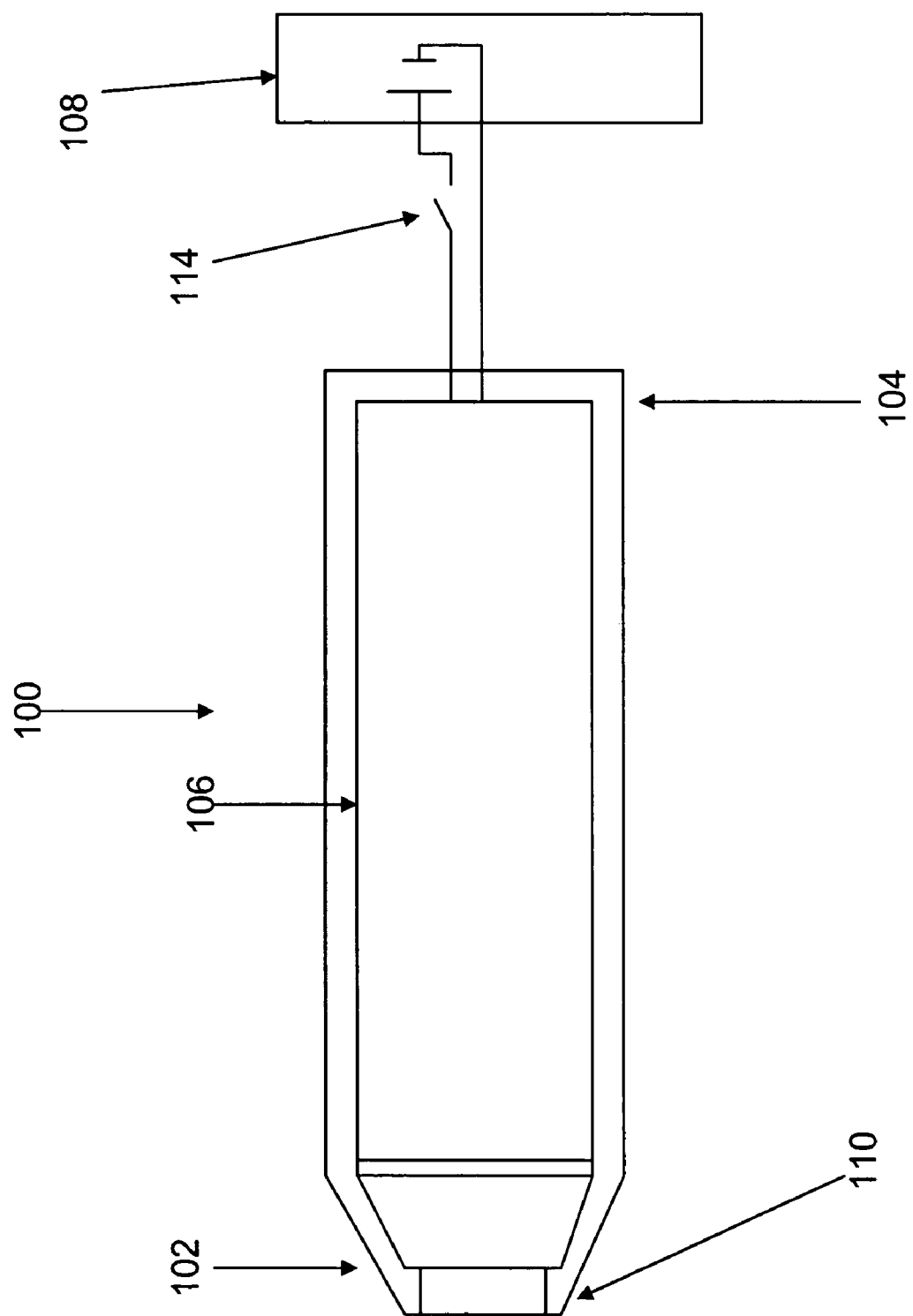
FIG. 1 shows a cross-sectional view of a device used to deliver antiparkinson drug aerosols to a mammal through an inhalation route.

"Aerodynamic diameter" of a given particle refers to the diameter of a spherical droplet with a density of 1 g/mL (the density of water) that has the same settling velocity as the given particle.

"Aerosol" refers to a suspension of solid or liquid particles in a gas.

"Aerosol drug mass density" refers to the mass of an antiparkinson drug per unit volume of aerosol.

"Aerosol mass density" refers to the mass of particulate matter per unit volume of aerosol.

"Aerosol particle density" refers to the number of particles per unit volume of aerosol.

"Amantadine" refers to tricyclo[3.3.1.1$^{3,7}$]decan-1-amine.

"Amantadine degradation product" refers to a compound resulting from a chemical modification of amantadine. The modification, for example, can be the result of a thermally or photochemically induced reaction. Such reactions include, without limitation, oxidation and hydrolysis. An example of a degradation product is nitroso-adamantane.

"Amorphous particle" refers to a particle that does not contain more than 50 percent by weight of a crystalline form. Preferably, the particle does not contain more than 25 percent by weight of a crystalline form. More preferably, the particle does not contain more than 10 percent by weight of a crystalline form.

"Antiparkinson drug degradation product" refers to a compound resulting from a chemical modification of an antiparkinson drug. The modification, for example, can be the result of a thermally or photochemically induced reaction. Such reactions include, without limitation, oxidation and hydrolysis.

"Benzotropine" refers to 3-(diphenylmethoxy)-8-methyl-8-azabicyclo[3.2.1]-octane.

"Benzotropine degradation product" refers to a compound resulting from a chemical modification of benzotropine. The modification, for example, can be the result of a thermally or photochemically induced reaction. Such reactions include, without limitation, oxidation and hydrolysis.

"Condensation aerosol" refers to an aerosol formed by vaporization of a substance followed by condensation of the substance into an aerosol.

"Deprenyl" refers to (R)-(−)-N,2-dimethyl-N-2-propynylphenethylamine.

"Deprenyl degradation product" refers to a compound resulting from a chemical modification of deprenyl. The modification, for example, can be the result of a thermally or photochemically induced reaction. Such reactions include, without limitation, oxidation and hydrolysis.

"Inhalable aerosol drug mass density" refers to the aerosol drug mass density produced by an inhalation device and delivered into a typical patient tidal volume.

"Inhalable aerosol mass density" refers to the aerosol mass density produced by an inhalation device and delivered into a typical patient tidal volume.

"Inhalable aerosol particle density" refers to the aerosol particle density of particles of size between 100 nm and 5 microns produced by an inhalation device and delivered into a typical patient tidal volume.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Pergolide" refers to 8-[(methylthio)methyl]-6-propylergoline.

"Pergolide degradation product" refers to a compound resulting from a chemical modification of pergolide. The modification, for example, can be the result of a thermally or photochemically induced reaction. Such reactions include, without limitation, oxidation and hydrolysis. An example of a degradation product is 3-nitrophthalic acid.

"Rate of aerosol formation" refers to the mass of aerosolized particulate matter produced by an inhalation device per unit time.

"Rate of inhalable aerosol particle formation" refers to the number of particles of size between 100 nm and 5 microns produced by an inhalation device per unit time.

"Rate of drug aerosol formation" refers to the mass of aerosolized antiparkinson drug produced by an inhalation device per unit time.

"Ropinerole" refers to 4-[2-(dipropylamino)-ethyl]-1,3-dihydro-2H-indol-2-one.

"Ropinerole degradation product" refers to a compound resulting from a chemical modification of ropinerole. The modification, for example, can be the result of a thermally or photochemically induced reaction. Such reactions include, without limitation, oxidation and hydrolysis.

"Settling velocity" refers to the terminal velocity of an aerosol particle undergoing gravitational settling in air.

"Typical patient tidal volume" refers to 1 L for an adult patient and 15 mL/kg for a pediatric patient.

"Vapor" refers to a gas, and "vapor phase" refers to a gas phase. The term "thermal vapor" refers to a vapor phase, aerosol, or mixture of aerosol-vapor phases, formed preferably by heating.

Formation of Antiparkinson Drug Containing Aerosols

Any suitable method is used to form the aerosols of the present invention. A preferred method, however, involves heating a composition comprising an antiparkinson drug to form a vapor, followed by cooling of the vapor such that it condenses to provide an antiparkinson drug comprising aerosol (condensation aerosol). The composition is heated in one of four forms: as pure active compound (e.g., pure benzotropine, pergolide, ropinerole, amantadine or deprenyl); as a mixture of active compound and a pharmaceutically acceptable excipient; as a salt form of the pure active compound; and, as a mixture of active compound salt form and a pharmaceutically acceptable excipient.

Salt forms of antiparkinson drugs (e.g., benzotropine, pergolide, ropinerole, amantadine or deprenyl) are either commercially available or are obtained from the corresponding free base using well known methods in the art. A variety of pharmaceutically acceptable salts are suitable for aerosolization. Such salts include, without limitation, the following: hydrochloric acid, hydrobromic acid, acetic acid, maleic acid, formic acid, and fumaric acid salts.

Pharmaceutically acceptable excipients may be volatile or nonvolatile. Volatile excipients, when heated, are concurrently volatilized, aerosolized and inhaled with the antiparkinson drug. Classes of such excipients are known in the art and include, without limitation, gaseous, supercritical fluid, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Solid supports on which the composition is heated are of a variety of shapes. Examples of such shapes include, without limitation, cylinders of less than 1.0 mm in diameter, boxes of less than 1.0 mm thickness and virtually any shape permeated by small (e.g., less than 1.0 mm-sized) pores. Preferably, solid supports provide a large surface to volume ratio (e.g., greater than 100 per meter) and a large surface to mass ratio (e.g., greater than 1 cm$^2$ per gram).

A solid support of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials are used to construct the solid supports. Classes of such materials include, without limitation, metals, inorganic materials, carbonaceous materials and polymers. The following are examples of the material classes: aluminum, silver, gold, stainless steel, copper and tungsten; silica, glass, silicon and alumina; graphite, porous carbons, carbon yams and carbon felts; polytetrafluoroethylene and polyethylene glycol. Combinations of materials and coated variants of materials are used as well.

Where aluminum is used as a solid support, aluminum foil is a suitable material. Examples of silica, alumina and silicon based materials include amphorous silica S-5631 (Sigma, St. Louis, Mo.), BCR171 (an alumina of defined surface area greater than 2 m$^2$/g from Aldrich, St. Louis, Mo.) and a silicon wafer as used in the semiconductor industry. Carbon yams and felts are available from American Kynol, Inc., New York, N.Y. Chromatography resins such as octadecycl silane chemically bonded to porous silica are exemplary coated variants of silica.

The heating of the antiparkinson drug compositions is performed using any suitable method. Examples of methods by which heat can be generated include the following: passage of current through an electrical resistance element; absorption of electromagnetic radiation, such as microwave or laser light; and, exothermic chemical reactions, such as exothermic solvation, hydration of pyrophoric materials and oxidation of combustible materials.

Delivery of Antiparkinson Drug Containing Aerosols

Antiparkinson drug containing aerosols of the present invention are delivered to a mammal using an inhalation device. Where the aerosol is a condensation aerosol, the device has at least three elements: an element for heating an antiparkinson drug containing composition to form a vapor; an element allowing the vapor to cool, thereby providing a condensation aerosol; and, an element permitting the mammal to inhale the aerosol. Various suitable heating methods are described above. The element that allows cooling is, in it simplest form, an inert passageway linking the heating means to the inhalation means. The element permitting inhalation is an aerosol exit portal that forms a connection between the cooling element and the mammal's respiratory system.

One device used to deliver the antiparkinson drug containing aerosol is described in reference to FIG. 1. Delivery device 100 has a proximal end 102 and a distal end 104, a heating module 106, a power source 108, and a mouthpiece 110. An antiparkinson drug composition is deposited on a surface 112 of heating module 106. Upon activation of a user activated switch 114, power source 108 initiates heating of heating module 106 (e.g, through ignition of combustible fuel or passage of current through a resistive heating element). The antiparkinson drug composition volatilizes due to the heating of heating module 106 and condenses to form a condensation aerosol prior to reaching the mouthpiece 110 at the proximal end of the device 102. Air flow traveling from the device distal end 104 to the mouthpiece 110 carries the condensation aerosol to the mouthpiece 110, where it is inhaled by the mammal.

Devices, if desired, contain a variety of components to facilitate the delivery of antiparkinson containing aerosols. For instance, the device may include any component known in the art to control the timing of drug aerosolization relative to inhalation (e.g., breath-actuation), to provide feedback to patients on the rate and/or volume of inhalation, to prevent excessive use (i.e., "lock-out" feature), to prevent use by unauthorized individuals, and/or to record dosing histories.

Dosage of Antiparkinson Drug Containing Aerosols

The dosage amount of antiparkinson drugs in aerosol form is generally no greater than twice the standard dose of the drug given orally. For instance, benzotropine, pergolide, ropinerole, amantadine and deprenyl are given orally at strengths of 0.5 mg to 2 mg, 0.05 mg to 1.0 mg, 0.25 mg to 4 mg, 50 mg to 100 mg, and 5 mg respectively for the treatment of Parkinsons. As aerosols, 0.1 mg to 4 mg of benztropine, 0.01 mg to 2.5 mg of pergolide, 0.02 mg to 4 mg of ropinerole, 5 mg to 250 mg of amantadine, and 0.5 mg to 12.5 mg of deprenyl are generally provided per inspiration for the same indication. A typical dosage of an antiparkinson drug aerosol is either administered as a single inhalation or as a series of inhalations taken within an hour or less (dosage equals sum of inhaled amounts). Where the drug is administered as a series of inhalations, a different amount may be delivered in each inhalation.

One can determine the appropriate dose of antiparkinson drug containing aerosols to treat a particular condition using methods such as animal experiments and a dose-finding (Phase I/II) clinical trial. One animal experiment involves measuring plasma concentrations of drug in an animal after its exposure to the aerosol. Mammals such as dogs or primates are typically used in such studies, since their respiratory systems are similar to that of a human. Initial dose levels for testing in humans is generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered.

Analysis of Antiparkinson Drug Containing Aerosols

Purity of an antiparkinson drug containing aerosol is determined using a number of methods, examples of which are described in Sekine et al., *Journal of Forensic Science* 32:1271–1280 (1987) and Martin et al., *Journal of Analytic Toxicology* 13:158–162 (1989). One method involves forming the aerosol in a device through which a gas flow (e.g., air flow) is maintained, generally at a rate between 0.4 and 60 L/min. The gas flow carries the aerosol into one or more traps. After isolation from the trap, the aerosol is subjected to an analytical technique, such as gas or liquid chromatography, that permits a determination of composition purity.

A variety of different traps are used for aerosol collection. The following list contains examples of such traps: filters; glass wool; impingers; solvent traps, such as dry ice-cooled ethanol, methanol, acetone and dichloromethane traps at various pH values; syringes that sample the aerosol; empty, low-pressure (e.g., vacuum) containers into which the aerosol is drawn; and, empty containers that fully surround and enclose the aerosol generating device. Where a solid such as glass wool is used, it is typically extracted with a solvent such as ethanol. The solvent extract is subjected to analysis rather than the solid (i.e., glass wool) itself. Where a syringe or container is used, the container is similarly extracted with a solvent.

The gas or liquid chromatograph discussed above contains a detection system (i.e., detector). Such detection systems are well known in the art and include, for example, flame ionization, photon absorption and mass spectrometry detectors. An advantage of a mass spectrometry detector is that it can be used to determine the structure of antiparkinson drug degradation products.

Particle size distribution of an antiparkinson drug containing aerosol is determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies.

Inhalable aerosol mass density is determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the tidal volume of an inhaling patient.

Inhalable aerosol drug mass density is determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the tidal volume of an inhaling patient. The amount of active drug compound collected in the chamber is determined by extracting the chamber, conducting chromatographic analysis of the extract and comparing the results of the chromatographic analysis to those of a standard containing known amounts of drug.

Inhalable aerosol particle density is determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size is determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$\pi$*$D^3$*$\phi$/6, where D is a typical particle diameter in the size range (generally, the mean boundary MMADs defining the size range) in microns, $\phi$ is the particle density (in g/mL) and mass is given in units of picograms ($g^{-12}$).

Rate of inhalable aerosol particle formation is determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 100 nm to 5 micron particles collected divided by the duration of the collection time.

Rate of aerosol formation is determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation is determined, for example, by delivering an antiparkinson drug containing aerosol into a confined chamber via an inhalation device over a set period of time (e.g., 3 s). Where the aerosol is pure antiparkinson drug, the amount of drug collected in the chamber is measured as described above. The rate of drug aerosol formation is equal to the amount of antiparkinson drug collected in the chamber divided by the duration of the collection time. Where the antiparkinson drug containing aerosol comprises a pharmaceutically acceptable excipient, multiplying the rate of aerosol formation by the percentage of antiparkinson drug in the aerosol provides the rate of drug aerosol formation.

Utility of Antiparkinson Drug Containing Aerosols

The antiparkinson drug containing aerosols of the present invention are typically used for the treatment of Parkinsons.

The following examples are meant to illustrate, rather than limit, the present invention.

Benztropine mesylate, pergolide mesylate and amantadine were purchased from Sigma (www.sigma-aldrich.com). Deprenyl hydrochloride was purchased from Sigma RBI (www.sigma-aldrich.com). Ropinerole hydrochloride was purchased as REQUIP® tablets from a pharmacy. Other antiparkinson drugs can be similarly obtained.

EXAMPLE 1

General Procedure for Obtaining Free Base for a Compound Salt

Approximately 1 g of salt (e.g., mono hydrochloride) is dissolved in deionized water (~30 mL). Three equivalents of sodium hydroxide (1 N $NaOH_{aq}$) is added dropwise to the solution, and the pH is checked to ensure it is basic. The aqueous solution is extracted four times with dichloromethane (~50 mL), and the extracts are combined, dried ($Na_2SO_4$) and filtered. The filtered organic solution is concentrated using a rotary evaporator to provide the desired free base. If necessary, purification of the free base is performed using standard methods such as chromatography or recrystallization.

EXAMPLE 2

General Procedure for Volatilizing Compounds from Halogen Bulb

A solution of drug in approximately 120 μL dichloromethane is coated on a 3.5 cm×7.5 cm piece of aluminum foil (precleaned with acetone). The dichloromethane is allowed to evaporate. The coated foil is wrapped around a 300 watt halogen tube (Feit Electric Company, Pico Rivera, Calif.), which is inserted into a glass tube sealed at one end with a rubber stopper. Running 90 V of alternating current (driven by line power controlled by a variac) through the bulb for 3.5 s (drug coating of 0.01 mg to 8 mg; assuming a drug density of about 1 g/cc, calculated thicknesses of the coatings on the 26.25 cm² aluminum solid support, after solvent evaporation, is about 0.004 microns to 3.0 microns ) or for 5 s (drug coating >8 mg) affords thermal vapor (including aerosol), which is collected on the glass tube walls. Reverse-phase HPLC analysis with detection by absorption of 225 nm light is used to determine the purity of the aerosol. (When desired, the system is flushed through with argon prior to volatilization.) To obtain higher purity aerosols, one can coat a lesser amount of drug, yielding a thinner film to heat. A linear decrease in film thickness is associated with a linear decrease in impurities.

Table 1, which follows, provides data from drugs volatilized using the above-recited general procedure.

TABLE 1

| Compound | Aerosol Purity | Argon Used |
| --- | --- | --- |
| Benztropine | 98.3% | No |
|  | 99.5% | Yes |
| Pergolide | 98% | No |
|  | 98% | Yes |
| Ropinerole | >90% | Yes |
| Amantadine | 100% | No |
|  | 100% | Yes |
| Deprenyl | 100% | No |
|  | 97% | Yes |

EXAMPLE 3

Particle Size, Particle Density, and Rate of Inhalable Particle Formation of Pergolide Aerosol A solution of 1.3 mg pergolide in 100 μL dichloromethane was spread out in a thin layer on the central portion of a 3.5 cm×7 cm sheet of aluminum foil. The dichloromethane was allowed to evaporate. Assuming a drug density of about 1 g/cc, the calculated thickness of the pergolide thin layer on the 24.5 cm² aluminum solid support, after solvent evaporation, is about 0.5 microns. The aluminum foil was wrapped around a 300 watt halogen tube, which was inserted into a T-shaped glass tube. Both of the openings of the tube were left open and the third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within 1 s, an aerosol appeared and was drawn into the 1 L flask by use of the piston, with collection of the aerosol terminated after 6 s. The aerosol was analyzed by connecting the 1 L flask to an eight-stage Andersen nonviable cascade impactor. Results are shown in table 1. MMAD of the collected aerosol was 1.8 microns with a geometric standard deviation of 2.2. Also shown in table 1 is the number of particles collected on the various stages of the cascade impactor, given by the mass collected on the stage divided by the mass of a typical particle trapped on that stage. The mass of a single particle of diameter D is given by the volume of the particle, $\pi D^3/6$, multiplied by the density of the drug (taken to be 1 g/cm³). The inhalable aerosol particle density is the sum of the numbers of particles collected on impactor stages 3 to 8 divided by the collection volume of 1 L, giving an inhalable aerosol particle density of $6.7 \times 10^6$ particles/mL. The rate of inhalable aerosol particle formation is the sum of the numbers of particles collected on impactor stages 3 through 8 divided by the formation time of 6 s, giving a rate of inhalable aerosol particle formation of $1.1 \times 10^9$ particles/second.

TABLE 1

Determination of the characteristics of a pergolide condensation aerosol by cascade impaction using an Andersen 8-stage non-viable cascade impactor run at 1 cubic foot per minute air flow.

| Stage | Particle size range (microns) | Average particle size (microns) | Mass collected (mg) | Number of particles |
|---|---|---|---|---|
| 0 | 9.0–10.0 | 9.5 | 0.01 | $1.3 \times 10^4$ |
| 1 | 5.8–9.0 | 7.4 | 0.02 | $7.5 \times 10^4$ |
| 2 | 4.7–5.8 | 5.25 | 0.03 | $3.6 \times 10^5$ |
| 3 | 3.3–4.7 | 4.0 | 0.06 | $1.9 \times 10^6$ |
| 4 | 2.1–3.3 | 2.7 | 0.10 | $9.8 \times 10^6$ |
| 5 | 1.1–2.1 | 1.6 | 0.19 | $8.8 \times 10^7$ |
| 6 | 0.7–1.1 | 0.9 | 0.09 | $2.5 \times 10^8$ |
| 7 | 0.4–0.7 | 0.55 | 0.04 | $4.0 \times 10^8$ |
| 8 | 0–0.4 | 0.2 | 0.03 | $6.0 \times 10^9$ |

EXAMPLE 4

Drug Mass Density and Rate of Drug Aerosol Formation of Pergolide Aerosol

A solution of 1.0 mg pergolide in 100 μL dichloromethane was spread out in a thin layer on the central portion of a 3.5 cm×7 cm sheet of aluminum foil. The dichloromethane was allowed to evaporate. Assuming a drug density of about 1 g/cc, the calculated thickness of the pergolide thin layer on the 24.5 cm² aluminum solid support, after solvent evaporation, is about 0.4 microns. The aluminum foil was wrapped around a 300 watt halogen tube, which was inserted into a T-shaped glass tube. Both of the openings of the tube were left open and the third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within seconds, an aerosol appeared and was drawn into the 1 L flask by use of the piston, with formation of the aerosol terminated after 6 s. The aerosol was allowed to sediment onto the walls of the 1 L flask for approximately 30 minutes. The flask was then extracted with acetonitrile and the extract analyzed by HPLC with detection by light absorption at 225 nm. Comparison with standards containing known amounts of pergolide revealed that 0.3 mg of >99% pure pergolide had been collected in the flask, resulting in an aerosol drug mass density of 0.3 mg/L. The aluminum foil upon which the pergolide had previously been coated was weighed following the experiment. Of the 1.0 mg originally coated on the aluminum, 1.0 mg of the material was found to have aerosolized in the 6 s time period, implying a rate of drug aerosol formation of 0.2 mg/s.

The invention claimed is:

1. A condensation aerosol for delivery of a drug selected from the group consisting of benzotropine, pergolide, amantadine, deprenyl and ropinerole, wherein the condensation aerosol is formed by heating a thin layer containing the drug, on a solid support, to produce a vapor of the drug, and condensing the vapor to form a condensation aerosol characterized by less than 10% drug degradation products by weight, and an MMAD of less than 5 microns.

2. The condensation aerosol according to claim 1, wherein the condensation aerosol is formed at a rate greater than $10^9$ particles per second.

3. The condensation aerosol according to claim 2, wherein the condensation aerosol is formed at a rate greater than $10^{10}$ particles per second.

4. The condensation aerosol according to claim 1, wherein the condensation aerosol is characterized by less than 2.5% drug degradation products by weight.

5. A method of producing a drug selected from the group consisting of benzotropine, pergolide, amantadine, deprenyl and ropinerole in an aerosol form comprising:
   a. heating a thin layer containing the drug, on a solid support, to produce a vapor of the drug, and
   b. providing an air flow through the vapor to form a condensation aerosol characterized by less than 10% drug degradation products by weight, and an MMAD of less than 5 microns.

6. The method according to claim 5, wherein the condensation aerosol is formed at a rate greater than $10^9$ particles per second.

7. The method according to claim 6, wherein the condensation aerosol is formed at a rate greater than $10^{10}$ particles per second.

8. The condensation aerosol according to claim 1, wherein the condensation aerosol is characterized by an MMAD of 0.1 to 5 microns.

9. The condensation aerosol according to claim 1, wherein the condensation aerosol is characterized by an MMAD of less than 3 microns.

10. The condensation aerosol according to claim 1, wherein the condensation aerosol is characterized by an MMAD of about 0.2 to about 3 microns.

11. The condensation aerosol according to claim 1, wherein the condensation aerosol is characterized by less than 5% drug degradation products by weight.

12. The condensation aerosol according to claim 1, wherein the thin layer contains at least 80% drug by weight.

13. The condensation aerosol according to claim 12, wherein the thin layer contains at least 95% drug by weight.

14. The condensation aerosol according to claim 1, wherein the condensation aerosol comprises at least 80% drug by weight.

15. The condensation aerosol according to claim 14, wherein the condensation aerosol comprises at least 95% drug by weight.

16. The condensation aerosol according to claim 1, wherein the thin layer has a thickness between 0.004 and 3 microns.

17. The condensation aerosol according to claim 1, wherein the solid support has the surface texture of a metal foil.

18. The condensation aerosol according to claim 1, wherein the solid support is a metal foil.

19. The condensation aerosol according to claim 1, wherein the drug is benzotropine.

20. The condensation aerosol according to claim 1, wherein the drug is pergolide.

21. The method according to claim 5, wherein the condensation aerosol is characterized by an MMAD of about 0.2 to 3 microns.

22. The condensation aerosol according to claim 1, wherein the drug is deprenyl.

23. The condensation aerosol according to claim 1, wherein the drug is ropinerole.

24. The method according to claim 5, wherein the condensation aerosol is characterized by an MMAD of 0.1 to 5 microns.

25. The method according to claim 5, wherein the condensation aerosol is characterized by an MMAD of less than 3 microns.

26. The method according to claim 25, wherein the condensation aerosol is characterized by an MMAD of about 0.2 to about 3 microns.

27. The method according to claim 5, wherein the condensation aerosol is characterized by less than 5% drug degradation products by weight.

28. The method according to claim 27, wherein the condensation aerosol is characterized by less than 2.5% drug degradation products by weight.

29. The method according to claim 5, wherein the thin layer contains at least 80% drug by weight.

30. The method according to claim 29, wherein the thin layer contains at least 95% drug by weight.

31. The method according to claim 5, wherein the condensation aerosol comprises at least 80% drug by weight.

32. The method according to claim 31, wherein the condensation aerosol comprises at least 95% drug by weight.

33. The method according to claim 5, wherein the thin layer has a thickness between 0.004 and 3 microns.

34. The method according to claim 5, wherein the solid support has the surface texture of a metal foil.

35. The method according to claim 5, wherein the solid support is a metal foil.

36. A method of producing benzotropine in an aerosol form comprising:
   a. heating a thin layer containing benzotropine, on a solid support, to produce a vapor of benzotropine, and
   b. providing an air flow through the vapor to form a condensation aerosol characterized by less than 5% benzotropine degradation products by weight, and an MMAD of about 0.2 and about 3 microns.

37. A method of producing pergolide in an aerosol form comprising:
   a. heating a thin layer containing pergolide, on a solid support, to produce a vapor of pergolide, and
   b. providing an air flow through the vapor to form a condensation aerosol characterized by less than 5% pergolide degradation products by weightm and an MMAD of about 0.2 and about 3 microns.

38. A method of producing amantadine in an aerosol form comprising:
   a. heating a thin layer containing amantadine, on a solid support, to produce a vapor of amantadine, and
   b. providing an air flow through the vapor to form a condensation aerosol characterized by less than 5% amantadine degradation products by weight, and an MMAD of about 0.2 and about 3 microns.

39. A method of producing deprenyl in an aerosol form comprising:
   a. heating a thin layer containing deprenyl, on a solid support, to produce a vapor of deprenyl, and
   b. providing an air flow through the vapor to form a condensation aerosol characterized by less than 5% deprenyl degradation products by weight, and an MMAD of about 0.2 and about 3 microns.

40. A method of producing ropinerole in an aerosol form comprising:
   a. heating a thin layer containing ropinerole, on a solid support, to produce a vapor of ropinerole, and
   b. providing an air flow through the vapor to form a condensation aerosol characterized by less than 5% ropinerole degradation products by weight, and an MMAD of about 0.2 and about 3 microns.

* * * * *